United States Patent
Bormann et al.

(10) Patent No.: US 9,562,008 B2
(45) Date of Patent: Feb. 7, 2017

(54) PROCESS FOR THE RECOVERY OF ε-CAPROLACTAM FROM EXTRACT WATER

(71) Applicant: Technip Zimmer GmbH, Frankfurt (DE)

(72) Inventors: Andreas Bormann, Frankfurt (DE); Manfred Albrecht, Bruchköbel (DE); Franz Samlitschka, Maintal (DE)

(73) Assignee: Technip Zimmer GmbH, Frankfurt (DE)

(*) Notice: Subject to any disclaimer, the term of this patent is extended or adjusted under 35 U.S.C. 154(b) by 0 days.

(21) Appl. No.: 14/917,808

(22) PCT Filed: Jul. 7, 2014

(86) PCT No.: PCT/EP2014/064462
§ 371 (c)(1),
(2) Date: Mar. 9, 2016

(87) PCT Pub. No.: WO2015/004062
PCT Pub. Date: Jan. 15, 2015

(65) Prior Publication Data
US 2016/0221943 A1    Aug. 4, 2016

(30) Foreign Application Priority Data
Jul. 9, 2013  (DE) .................. 10 2013 107 238

(51) Int. Cl.
*C07D 201/16*   (2006.01)
(52) U.S. Cl.
CPC .................. *C07D 201/16* (2013.01)
(58) Field of Classification Search
CPC .................................................. C07D 201/16
See application file for complete search history.

(56) References Cited

U.S. PATENT DOCUMENTS

| | | | |
|---|---|---|---|
| 4,053,457 A | 10/1977 | Cordes et al. | |
| 4,107,160 A | 8/1978 | Dicoi et al. | |
| 5,218,080 A | 6/1993 | Dellinger | |
| 5,653,889 A | 8/1997 | Buchanan | |
| 6,093,788 A * | 7/2000 | Born ................. | B01D 1/26 |
| | | | 528/310 |

FOREIGN PATENT DOCUMENTS

| | | |
|---|---|---|
| DE | 4316408 | 11/1994 |
| DE | 19622780 | 12/1996 |
| DE | 19753377 | 6/1999 |
| EP | 0000397 | 1/1979 |
| EP | 0771834 | 5/1997 |
| JP | 2007099646 | 4/2007 |
| NL | 7600212 | 7/1976 |
| WO | 03045911 | 6/2003 |

OTHER PUBLICATIONS

International Search Report for international application No. PCT/EP2014/064462, dated Oct. 23, 2014 (3 pages).

* cited by examiner

*Primary Examiner* — Bruck Kifle
(74) *Attorney, Agent, or Firm* — Hamre, Schumann, Mueller & Larson, P.C.

(57) ABSTRACT

A process for the recovery of ε-caprolactam from extract water of polycaprolactam obtained by hydrolytic polymerization, wherein the extract water is concentrated, subsequently contained oligomers are depolymerized, non-depolymerizable impurities are separated, water and low-boiling impurities are removed, wherein for adjusting the purity of the recovered ε-caprolactam and the energy consumption used for the process a part of the product is removed from the process as intermediate products.

3 Claims, 1 Drawing Sheet

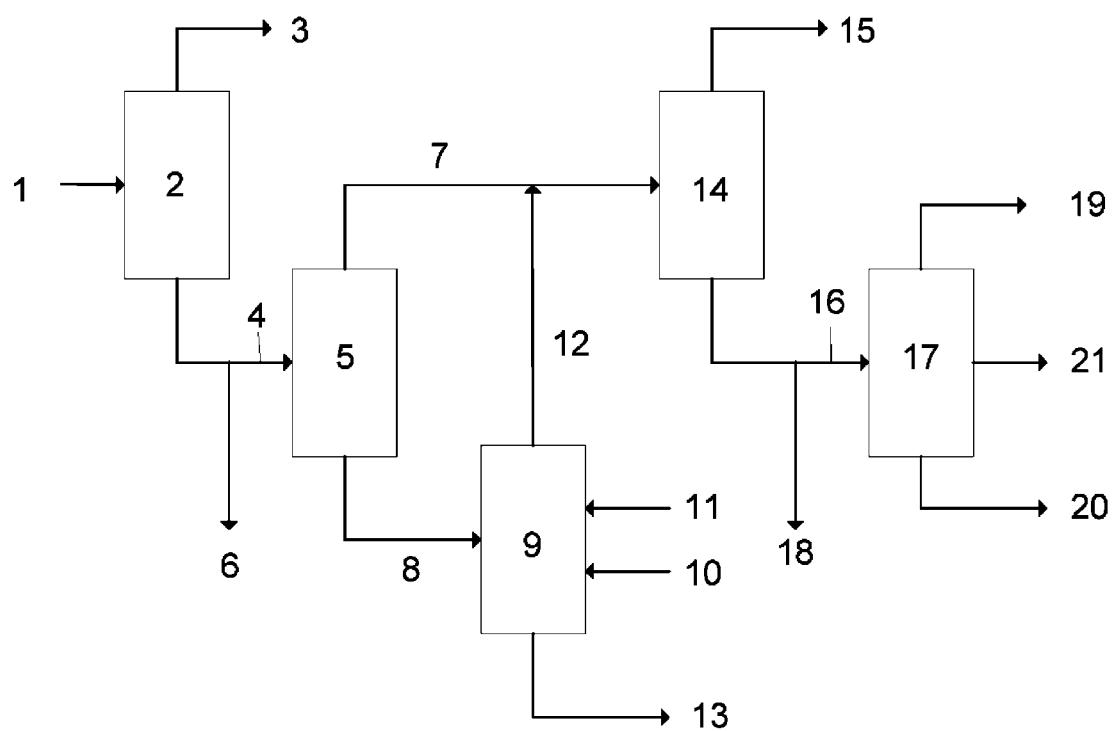

PROCESS FOR THE RECOVERY OF ε-CAPROLACTAM FROM EXTRACT WATER

FIELD OF THE INVENTION

The invention relates to a process for the recovery of ε-caprolactam from extract water of polycaprolactam obtained by hydrolytic polymerization.

Furthermore, the invention relates to the use of the intermediate and end product streams obtained in the process according to the invention.

PRIOR ART

The polymerization of ε-caprolactam to polycaprolactam, which also is referred to as polyamide 6, PA6 or nylon 6, in practice is carried out up to a reaction equilibrium at which approximately 10 wt-% of the reaction mass still are present as monomer, i.e. as ε-caprolactam or ε-caprolactam oligomer. This non-polymerized fraction must be removed from the polymer, as it would disturb the further processing of the polymer to end products such as yarns, films or engineering plastics.

The removal of the mono- and oligomers from the polymer is effected by extraction by means of water, by forming a so-called extract water, cf. Ullmann's Encyclopedia of Industrial Chemistry, 6th Edition, Vol. 28, pp. 38, 39.

As it is a valuable raw material, attempts generally are made to again recirculate the ε-caprolactam monomers and oligomers dissolved in the extract water, the extract, into the polymerization process by admixing the same to the so-called fresh lactam, i.e. ε-caprolactam, which after its production has not yet been used for the polymerization.

A process for the recovery of the mono- and oligomers is known for example from the German patent specification DE 197 53 377 B4. It comprises the following process steps:
  a) By a single- or multistage distillation, the extract water is concentrated by separation of water;
  b) the concentrated extract water is separated by distillation into a vaporous ε-caprolactam-water phase and a liquid oligomer-ε-caprolactam phase;
  c) into the liquid oligomer-ε-caprolactam phase steam is introduced in the presence of a catalyst, wherein the oligomers are hydrolytically depolymerized to ε-caprolactam, and ε-caprolactam is stripped out of the phase by the steam, and wherein non-depolymerizable impurities are discharged from the process as bottom product;
  d) the vaporous ε-caprolactam-water phase formed in step b) and the ε-caprolactam-steam phase formed in step c) are combined to one phase, water is separated by distillation, and there is obtained a liquid ε-caprolactam phase poor in oligomers and water, which can be admixed to fresh lactam used for the polymerization of polyamide 6.

The purity requirements for the ε-caprolactam recovered from the extract water depend on the intended use of the polymer, to which it is to be polymerized as admixture to the used so-called fresh lactam not originating from a recovery. Too low a purity of the recovered ε-caprolactam leads to an increased number of malfunctions and hence to increased costs of polymer processing, and too high a purity leads to a high energy consumption in the recovery process and hence to an uneconomic mode of operation.

In the process according to DE 196 53 377 B4 it is disadvantageous that it cannot sufficiently flexibly react to both highest and also low requirements as to the purity of the recovered monomer.

Highest purity requirements cannot be satisfied, because highly volatile impurities, as they can be obtained in the depolymerization of the oligomers in process step c) and whose boiling temperatures lie above the boiling temperature of water, but below that of ε-caprolactam, cannot be removed from the monomer or ε-caprolactam phase in process step d).

On the other hand, the extract also passes through the energy-expensive process steps c) and d), when the purity requirements are low and a certain amount of oligomers and impurities would be admissible.

Therefore, it is the object of the present invention to provide a process in which the disadvantages of the prior art do not occur.

DESCRIPTION OF THE INVENTION

The object is solved by a process according to claim 1.

The process according to the invention is characterized by an improved adaptability to the purity requirements for the recovered ε-caprolactam as made by the polymer processing processes.

On the one hand, this is achieved in that the oligomer-free ε-caprolactam recovered from the extract water, which is treated in steps a) to d), is subjected to an additional distillation in which highly volatile impurities, whose boiling temperatures lie above the boiling temperature of water, but below that of ε-caprolactam, are separated. These highly volatile impurities can have been formed e.g. by thermally caused decomposition of ε-caprolactam in process step c), depolymerization.

On the other hand, the recovery process according to the invention can be operated in a very energy-saving manner, when low requirements are made as to the purity of the recovered ε-caprolactam.

When lower purity requirements are made, the process according to the invention provides for removing partly processed product from the process already after steps a) and d) as first and second intermediate product stream, respectively. The energy consumption in the succeeding processing steps thereby is lowered.

The recovered product each removed after steps a), d) and e) either can each be supplied to a particular polymerization process with the corresponding quality requirements for the recovered product and hence the economy of the recovery can be optimized by taking account of the required product quality, or these three partial product streams or end product streams are combined. In the latter case, the purity of the product and the energy consumption of the recovery process can be adjusted by the mixing ratio.

The invention also relates to the use of the intermediate and end product streams obtained in the process according to the invention. The first intermediate product stream preferably is used for the production of engineering plastics or carpet yarn, the second intermediate product stream preferably is used for the production of carpet yarn, pre-oriented yarn (POY), tire cord basic yarn or film, and the end product stream preferably is used for the production of fully drawn yarns (FDY). There can each be obtained specification-compliant products with optimized energy consumption at the same time.

EXEMPLARY EMBODIMENTS

Further developments, advantages and possible applications of the invention can also be taken from the following description of exemplary embodiments and numerical examples as well as the drawing. All features described form the invention per se or in any combination, independent of their inclusion in the claims or their back-reference.

With reference to the drawing, FIG. 1, the process will now be explained below.

FIG. 1 shows a block diagram of the process according to claim 1.

The extract water 1 produced in the extraction of polyamide 6, which is not shown in FIG. 1, is supplied to a distillation process 2. This distillation can be carried out in one or more stages. Water in the form of steam 3 is separated from the extract water 1. It can be recirculated into the extraction process for reuse. As bottom product concentrated extract water 4 is obtained, which is supplied to a further distillation process 5.

In this distillation process 5, the concentrated extract water is separated into a gaseous $\epsilon$-caprolactam-steam phase 7 and a liquid oligomer-$\epsilon$-caprolactam phase 8.

The oligomer-$\epsilon$-caprolactam phase 8 is supplied to a depolymerization process 9. In this process 9, the oligomers obtained in phase 8 are hydrolytically depolymerized to $\epsilon$-caprolactam by introducing steam 10 and a catalyst 11. As catalyst 11 phosphoric acid is often used. The $\epsilon$-caprolactam furthermore is stripped out of the oligomer-$\epsilon$-caprolactam phase by the steam and, shown as stream 12, supplied to a further distillation process 14 together with the $\epsilon$-caprolactam-water phase 7. The constituents of the oligomer-$\epsilon$-caprolactam not depolymerizable in process 9 are discharged from the process as bottom product 13 and disposed of as waste.

In the distillation process 14, water, in the form of steam, is separated from the phases 7 and 12 as top product 15, and as bottom product 16 $\epsilon$-caprolactam poor in water is obtained, which however still contains impurities. To separate the same, this phase 16 is introduced into a further distillation 17 which is carried out in at least two stages. The low-boiling impurities are separated in the first stage or stages as top product 19, and the high-boiling impurities are separated in the last stage as bottom product 20. The recovered, completely purified $\epsilon$-caprolactam end product is obtained as top product 21 of the last distillation stage.

To be able to also produce recovered $\epsilon$-caprolactam with lower purity and with lower energy consumption, product quantities, represented as stream 6 (first intermediate product stream) and 18 (second intermediate product stream), according to the invention can be branched off already from the concentrated extract water 4 and from the oligomer- and water-free $\epsilon$-caprolactam 16. These branched streams 6 and 18 can be mixed separately or with each other in a freely selectable ratio and can be supplied to a polymerization process.

LIST OF REFERENCE NUMERALS 1 extract water from extraction
2 distillation
3 steam
4 extract water, concentrated
5 distillation
6 extract water, concentrated (first intermediate product stream)
7 $\epsilon$-caprolactam-steam phase
8 oligomer-$\epsilon$-caprolactam phase
9 depolymerization process
10 steam
11 catalyst
12 $\epsilon$-caprolactam-steam phase
13 non-depolymerizable impurities
14 distillation
15 steam
16 oligomer- and water-free $\epsilon$-caprolactam
17 distillation
18 oligomer- and water-free $\epsilon$-caprolactam (second intermediate product stream)
19 low-boiling impurities
20 high-boiling impurities
21 purified $\epsilon$-caprolactam (end product stream)

The invention claimed is:

1. A process for the recovery of $\epsilon$-caprolactam from extract water of polycaprolactam obtained by hydrolytic polymerization, comprising the following process steps:
   a. by single- or multistage distillation the extract water is concentrated by separation of water, wherein a first intermediate product stream is obtained, whose concentration of $\epsilon$-caprolactam is increased with respect to the extract water;
   b. the first intermediate product stream is separated by distillation into a first vaporous $\epsilon$-caprolactam-water phase and a liquid oligomer-$\epsilon$-caprolactam phase;
   c. into the liquid oligomer-$\epsilon$-caprolactam phase steam is introduced in the presence of a catalyst, wherein the $\epsilon$-caprolactam oligomers are hydrolytically depolymerized to monomeric $\epsilon$-caprolactam, and $\epsilon$-caprolactam is stripped out of the phase by the steam, wherein a second vaporous $\epsilon$-caprolactam-water phase is obtained and wherein non-depolymerizable impurities are discharged from the process as bottom product;
   d. the first vaporous $\epsilon$-caprolactam-water phase formed in step b) and the second $\epsilon$-caprolactam-steam phase formed in step c) are combined to a unified $\epsilon$-caprolactam-water phase, from which water is separated by distillation and thus an oligomer- and water-free $\epsilon$-caprolactam phase is obtained as second intermediate product stream;
   wherein the $\epsilon$-caprolactam phase obtained in step d) as second intermediate product stream is supplied to a distillation comprising at least two stages in a further step e), wherein an end product stream depleted of highly volatile impurities is obtained, and that at least a part of the first intermediate product stream and/or the second intermediate product stream is discharged from the process.

2. The process according to claim 1, wherein the first intermediate product stream, the second intermediate product stream and the end product stream are combined to a unified product stream.

3. The process according to claim 1, wherein phosphoric acid is used as a catalyst in step c) of claim 1.

* * * * *